United States Patent [19]

Ilsink

[11] Patent Number: Plant 7,368

[45] Date of Patent: Oct. 30, 1990

[54] ROSE PLANT INTERLIEN

[75] Inventor: Peter Ilsink, Leersum, Netherlands

[73] Assignee: Jackson & Perkins Company, Medford, Oreg.

[21] Appl. No.: 321,905

[22] Filed: Mar. 10, 1989

[51] Int. Cl.[5] ..... A01H 5/00

[52] U.S. Cl. ..... Plt./26

[58] Field of Search ..... Plt. 26

*Primary Examiner*—Howard J. Locker

*Attorney, Agent, or Firm*—Majestic, Parsons, Siebert & Hsue

[57] ABSTRACT

A rose variety of the Floribunda class is provided having good production of flowers in three to seven flower sprays, disease resistant foliage and vigorous upright growth habit.

1 Drawing Sheet

SUMMARY OF THE DISCOVERY

The present discovery relates to a new and distinct variety of rose plant of the Floribunda class, which was originated by me by crossing an unnamed seedling with another unnamed seedling. The female parent, an unnamed seedling derived from crossing the pink Floribunda "Poulsen's Pink" with a seedling miniature derived from an unnamed seedling of De Ruiter of Holland produces stems 30 cm long, has small foliage (each leaflet is 1 to 1.5 cm. long) and has very glossy foliage. The male parent, an unnamed seedling derived from the self-pollination of a Rosa Kordesi seeling, is a vigorous, upright, large leaved plant bearing pink flowers that are about 3.5 cm wide, in large sprays of 3 to 7 flowers per spray, on long (about 60 cm) stems.

The primary objective of this breeding was to produce a new rose variety of the Floribunda class ideally suited for use as a cut flower spray rose. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Good production of flowers in three to seven flower sprays.
2. Long vase life.
3. Disease resistant foliage.
4. Vigorous upright growth habit. The present discovery, Interlien, combines the glossy foliage, pink flowers and long vase life of the female parent with the longer stems, flowers borne in clusters and vigor of the male parent.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE DISCOVERY

The following is a detailed description of my new rose cultivar, which has been denominated "Interlien". Color terminology is in accordance with The Royal Horticultural Society Colour Chart except where an ordinary dictionary significance for the color is apparent.

Observations of the buds and flowers were made from specimens grown in a garden environment at Somis, Calif. from July through December.

FLOWER

The blooming habit is continuous. The bud size is three quarters of an inch when the petals start to unfurl. The bud form is a short pointed ovoid. The bud color when sepals first divide is near Red Group 37C; when half blown the upper side of petals is near Red Group 37C, and the lower side of petals is near Red Group 37C. The sepals have a color near Green Group 138A. The surface texture is covered in fine hairs. There are three lightly appendaged sepals, and two unappendaged sepals with hairy edge. The receptacle color is near Green Group 138A and of funnel shape, large size and smooth surface. The peduncle is of medium length and smooth surface. Penduncle color is medium green, and the peduncle is stiff and erect.

BLOOM

Bloom size is small, with an average open size of two to two and one half inches, borne several together, in clusters. The stems are strong and medium in length. The form when first opened is high center and retained to the end. The outer petals curl back. Under normal conditions there are 40 to 50 petals. The upper side of petals at the flower center is near Red Group 37C, and the reverse side of the petals is near Red Group 37C. The base of petals has a small whitish half moon at the point of attachment. The major color on the upper side is Red Group 37C.

The fragrance is slight. The petal texture is thick, of a notched, deltoid shape and the tips are slightly recurved.

The arrangement is imbricated with few petaloids in the center. The blooms drop off cleanly, and last both on the plant and as a cut flower for a long time.

Flowers have a vase life of about 7–9 days, which is considered long in the industry since a vase life of about 3–5 days is considered average and a vase life of about 5–7 days as good.

REPRODUCTIVE PARTS

There are many anthers of medium size, of yellow color and arranged regularly around the styles. The filaments are white, the pollen is lemon yellow, the styles are white and the stigmas are greenish white.

Because the variety is a forcing variety for use as a greenhouse cut flower, there has not been a determination made on hip formation; however, when artificially pollinated, small round hips (1.5–2.0 cm in diameter) form that turn yellow to orange on ripening.

PLANT

A bush growth of vigorous, upright and branching form.

Because this variety is a greenhouse cut flower variety, hardiness is not an issue; however, the plant will thrive in areas where winters do not go below about 25° F.

FOLIAGE

Small size, normal in quantity. The new foliage is reddish colored. The old foliage is dark glossy green. Normal mid-stem leaves have five leaflets.

The leaflets are of a pointed oval shape, are glossy and have a smooth texture with a serrated edge. The serration is single and small in size. Petiole rachis is green and petiole underside is rough with prickles. Stipules are short and bearded. The foliage is resistant to mildew under normal growing conditions at Somis, Calif.

The foliage is susceptible to black spot under severe conditions, but is typically very tolerant to this disease.

WOOD

New wood is light green, with a smooth bark. Old wood is green, with a smooth bark.

PRICKLES

There are an ordinary number of prickles on main canes from the base and on laterals from the main canes. The form is straight. There are no prickles on the main stalks or laterals, as these only occur on peduncles. Color when young is red.

PARENTAGE

The seed parent was an unnamed seedling. The pollen parent was also an unnamed seedling.

CLASSIFICATION

Botanical is Floribunda. Commerical is cut flower spray rose.

I claim:

1. A new and distinct variety of rose plant of the Floribunda class substantially as herein shown and described, characterized particularly as to novelty by its vigorous upright growth habit, glossy green disease resistant foliage, good production of flowers in sprays of three to seven flowers, and long vase life.

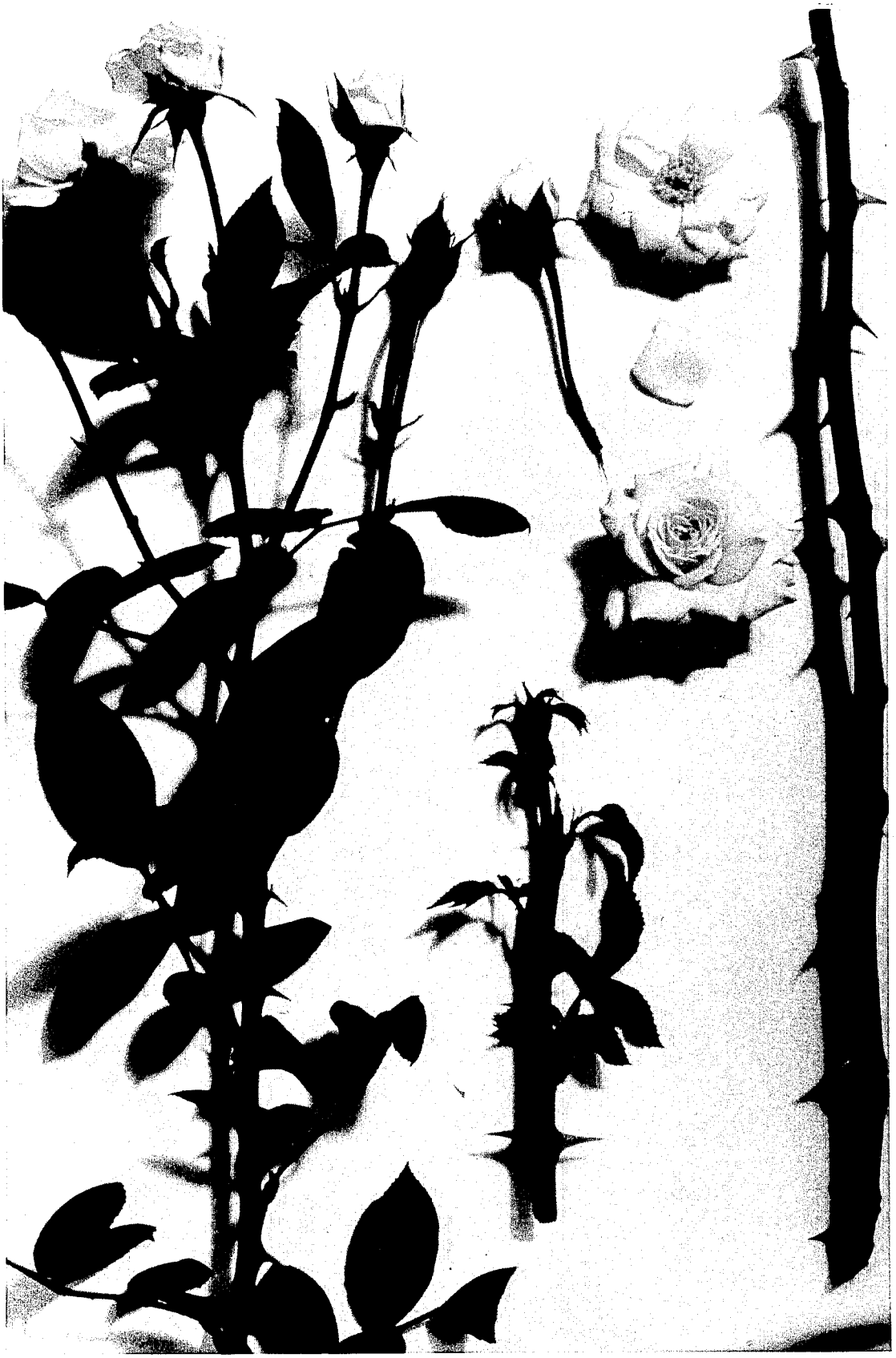

* * * * *